United States Patent [19]

Ihrman

[11] Patent Number: 4,611,045
[45] Date of Patent: Sep. 9, 1986

[54] MONOALKYLATION OF 1-ALKYL-DIAMINOBENZENES

[75] Inventor: Kryn G. Ihrman, Farmington, Mich.

[73] Assignee: Ethyl Corporation, Richmond, Va.

[21] Appl. No.: 583,752

[22] Filed: Feb. 27, 1984

Related U.S. Application Data

[63] Continuation of Ser. No. 427,139, Sep. 29, 1982, Pat. No. 4,440,952, which is a continuation-in-part of Ser. No. 403,289, Jul. 30, 1982, which is a continuation-in-part of Ser. No. 397,488, Jul. 12, 1982, abandoned.

[51] Int. Cl.$^4$ .............................................. C08G 18/32
[52] U.S. Cl. ........................................ 528/76; 528/64; 528/85
[58] Field of Search ............................ 528/76, 64, 85

[56] References Cited

U.S. PATENT DOCUMENTS 3,194,793 7/1965 Kogon ................................. 260/77.5
4,218,543 8/1980 Weber et al. ......................... 521/51
4,440,952 4/1984 Ihrman ................................. 564/305

Primary Examiner—Maurice J. Welsh
Attorney, Agent, or Firm—Donald L. Johnson; John F. Sieberth

[57] ABSTRACT

A process for monoalkylating 1-alkyl-2,4-diaminobenzene or 1-alkyl-2,6-diaminobenzene. Propylene is reacted with 2,4-diaminotoluene in the presence of aluminum anilide catalyst. Aniline is an optional ingredient. 1-Methyl-2,6-diamino-3-isopropylbenzene is a new compound:

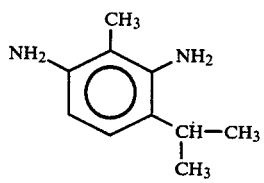

1 Claim, No Drawings

MONOALKYLATION OF 1-ALKYL-DIAMINOBENZENES

CROSS REFERENCE TO RELATED APPLICATIONS

This application is a continuation Ser. No. 427,139, filed Sept. 29, 1982 now U.S. Pat. No. 4,440,952, which is a continuation-in-part of application Ser. No. 403,289, filed July 30, 1982, which is a continuation-in-part of application Ser. No. 397,488, filed July 12, 1982, now abandoned.

BACKGROUND OF THE INVENTION

I. Field of the Invention

This invention relates to catalyzed alkylation of aromatic reactants in general and to monoalkylation of 1-alkyl-diaminobenzenes in particular.

II. Description of the Prior Art

There exists a need for new and varied dialkyl-diaminobenzenes for various uses. Such compounds are used as curing agents for epoxy resins, fuel stabilizers, antioxidants, hair dyes, and more recently as polyurethane chain extenders.

Various prior art alkylation techniques are disclosed in the following patents: U.S. Pat. Nos. 2,814,646; 3,275,690; 3,649,693; 3,678,113; 3,923,892; 4,128,582; and 4,219,502.

SUMMARY OF THE INVENTION

The present invention is directed to providing dialkyl-diaminobenzenes from alkyl-diaminobenzenes. The products have numerous direct uses as well as their utility as versatile intermediates.

The present invention is a process for the monoalkylation of 1-alkyl-2,4-diaminobenzene of structure:

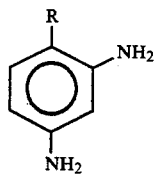

or 1-alkyl-2,6-diaminobenzene of structure:

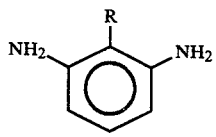

where R is a lower alkyl or cycloalkyl, said process comprising the steps of:
(a) reacting a 1-alkyl-2,4-diaminobenzene or a 1-alkyl-2,6-diaminobenzene at elevated temperature and pressure with an alkylene having at least three carbon atoms, in the presence of an aluminum anilide catalyst; and
(b) recovering a monoalkylated product of 1-alkyl-2,4-diaminobenzene or 1-alkyl-2,6-diaminobenzene as the principal product.

The present invention is also a process for the production of 1-methyl-2,4-diamino-5-ispropylbenzene comprising the steps of:
(a) heating about five mole parts 1-methyl-2,4-diaminobenzene, about one mole part aniline, and about one mole part aluminum anilide catalyst with propylene at about 300° C. and about 1,000 psig; and
(b) recovering 1-methyl-2,4-diamino-5-isopropylbenzene.

Alkylenes suitable for the invention include propylene, butylene, pentylene, cyclohexene and the like.

Catalysts suitable for the invention are those containing an active aluminum, preferably organoaluminums. Most preferred is triethylaluminum.

Any 2,4-diamino or 2,6-diamino alkylbenzene is suitable for the invention but the 2,4-diaminos are preferred because they provide a higher conversion. The alkyl substituent may be methyl, ethyl, or other lower alkyl/cycloalkyl substituent. Methyl is especially preferred. Most especially preferred is the reaction of propylene and 1-methyl-2,4-diaminobenzene.

Aniline is an optional ingredient. While Applicant does not fully understand the role of aniline in the reaction, it does provide catalyst stability. It is theorized that the aniline prevents polymerization of the organoaluminum catalyst since in some cases without aniline, the reaction mass becomes too viscous for good catalytic activity and te experiment must be scrapped. Applicant does not intend to be bound by this theory.

The present inventive process is carried out in the presence of an aluminum anilide-type catalyst. Aluminum anilide-type catalysts useful in the process include those used to ortho alkylate amines as described in U.S. Pat. Nos. 2,814,646; 3,275,690; 3,923,892; and 4,128,582. The aluminum anilides are readily prepared by reacting aluminum, aluminum hydride, aluminum alkyl halide, or preferably aluminum trialkyls such as the tri-lower alkyls including triethyl aluminum and trimethyl aluminum. This can be carried out by adding the aluminum or aluminum compound to aromatic amine and heating in a nitrogen atmosphere unitl an exothermic reaction occurs. This is preferably conducted in an autoclave which can withstand 1,000 psig pressure. Suitable aluminum alkyl halides include diethyl aluminum chloride, methyl aluminum sesquichloride, and the like When aluminum alkyls are used to prepare the catalyst care should be taken in handling these pyrophoric materials. The alkyls react with aromatic amines at fairly low temperatures, about ambient to 150° C. Aluminum metal generally requires a little higher temperature, about 200° C. or more. Catalyst formation, once initiated, proceeds rapidly.

The aluminum anilide-type catalysts also include combinations of the above with Friedel-Crafts promoters such as aluminum chloride or hydrogen halide promoters. Of the latter, hydrogen chloride is preferred. An amount sufficient to provide about 0.1–2.0 gram atoms chloride per gram atom aluminum is a useful ratio. The hydrogen halide is merely added to the aluminum anilide catalyst.

The amount of aluminum anilide-type catalyst used can vary over a wide range. A useful range is that amount which provides about 0.005—0.5 gram atom of aluminum per mole aromatic diamine to be alkylated. A more preferred range is about 0.1–0.25 gram atom aluminum per mole diamine.

The alkylation is carried out by adding the catalyst precursor to the diamine or mixture of diamines, optionally with aniline. This is heated under nitrogen in a sealed autoclave to form the catalyst. After the catalyst forms the autoclave is cooled and vented although venting is not required. The autoclave is then sealed and heated to an elevated reaction temperature. A useful range for carrying out the alkylation is about 200°–500° C. A preferred temperature is about 300°–400° C.

It is therefore an object of the present invention to provide a straightforward, relatively inexpensive process for the production of dialkyl-diaminobenzenes.

It is also an object of the present invention to provide the novel and useful compound 1-methyl-2,4-diamino-5-isopropylbenzene.

It is another object of this invention to provide an efficient alkylation process which doesn't require expensive catalysts such as platinum or silver.

It is still another object of this invention to provide monoalkylation of 1-alkyl-2,4-diaminobenzene and/or 1-alkyl-2,6-diaminobenzene in preference over dialkylation or trialkylation.

These and other objects of the present invention will be better understood by a reading of the following description of the best mode of the invention now known to me.

DESCRIPTION OF THE PREFERRED EMBODIMENT

The following non-limiting examples serve to illustrate the invention.

Example 1

Liquified propylene was drawn into a pressure burrette with a piston device. The filled pressure burrette was used to provide a measured amount of propylene at constant pressure to a one-liter autoclave fitted with a dropping funnel and adapter. The autoclave was charged with:

(a) 219.6 grams (1.8 moles) 2,4-diaminotoluene obtained from Aldrich Chemical Company and distilled;

(b) 41 grams (0.36 mole) triethylaluminum of Ethyl Corporation (added dropwise over 15 minutes); and (c) 33.5 grams (0.36 mole) aniline.

The dropping funnel and adapter were removed, the autoclave was sealed and heated to 150° C. for catalyst formation. The autoclave was allowed to cool and vented.

The autoclave was again sealed and heated to 300° C. as propylene was fed from the burrette at 1,000 psig. The propylene has a specific gravity of 0.5146 at 68° F. Samples of about 15 grams each were taken after one, three, and six hours. Analysis of the three samples is shown in Table 1.

TABLE 1

| | Propylation Of 2,4-Diaminotoluene | | | |
|---|---|---|---|---|
| Sample No. | % Aniline | % 2,4-Diamino-toluene | % Mono-propyl | % Dipropyl |
| 1 | 7 | 34 | 42 | — |
| 2 | 7 | 18 | 50 | 5 |
| 3 | 6 | 9 | 53 | 7 |

The reaction mass of 203 grams was discharged from the autoclave and hydrolyzed with 25% NaOH to convert the aluminum to a water soluble form. The organics were filtered hot to provide 187 grams product. The product was purified by distillation in a one-inch by 13-inch column packed with protruded stainless steel. Analysis by gas chromatography, NMR, and infrared spectroscopy confirmed that the principal product was 1-methyl-2,4-diamino-5-isopropylbenzene.

Example 2

The same procedure and stoichiometry was followed as in Example 1, but using 2,6-diaminotoluene. Samples were taken after one, two, four, and six and one-half hours. The analysis of these samples is presented in Table 2. The results demonstrate that the reaction must be controlled terminated early to preserve the monopropylated product as the principal product.

TABLE 2

| | Propylation Of 2,6-Diaminotoluene | | | |
|---|---|---|---|---|
| Sample No. | % Aniline | % 2,6-Diamino-toluene | % Mono-propyl | % Dipropyl |
| 1 | 8 | 20 | 45 | 21 |
| 2 | 8 | 8 | 37 | 41 |
| 3 | 7 | 5 | 18 | 63 |
| 4 | 7 | 6 | 11 | 69 |

The reaction mass of 264 grams was discharged from the autoclave and recovered as in Example 1 to provide 247 grams product which was purified by distillation.

Example 2A

Following the same procedure and proportions of materials as in Examples 1 and 2 (5:1:1) the process of the invention was carried out using a toluenediamine (TDA) stream having 80% 2,4-TDA and about 20% 2,6-TDA. The crude product was 10% aniline, 15% unreacted TDA, 53% mono-propyl TDA's and 12% dipropyl TDA's. The reaction mixture was hydrolyzed, flash distilled and then fractionated to remove unreacted TDA. The product was then flash distilled to provide 185 grams of the composition given in Table 3.

TABLE 3

| Propylation of Mixed TDA's | |
|---|---|
| 1-methyl-2,6-diamino-3-isopropylbenzene | 18% |
| 1-methyl-2,4-diamino-5-isopropylbenzene | 54% |
| 1-methyl-2,4-diamino-3,5-diisopropylbenzene | 8% |
| 1-methyl-2,6-diamino-3,5-diisopropylbenzene | 16.8% |
| 1-methyl-diamino-isopropyl-n-propylbenzene | 1.7% |

The first listed compound was confirmed to have the structure:

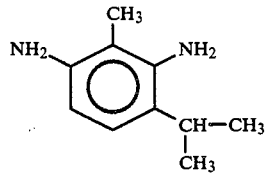

by gas chromatography, NMR, and infrared spectroscopy analyses.

Example 3

A small sample of the 1-methyl-2,4-diamino-5-isopropylbenzene component of the yield from Example 1 was tested as a polyurethane chain extender.

The following ingredients were used:
12.5 grams Jefferson 6503 polyol;
5.3 grams Upjohn Isonate 1431 MDI (polyisocyanate);

2.61 grams 1-methyl-2,4-diamino-5-isopropylbenzene;

1 drop of dibutyl tin dilaurate (catalyst).

The novel 1-methyl-2,4-diamino-5-isopropylbenzene and polyol were mixed, placed in an air circulated oven at 150° C. until homogeneous, and cooled to room temperature in a nitrogen bag. The one drop of catalyst was added and mixed. Finally, the MDI was quickly added and the mixture stirred by hand to form a hard polymer. The following times, indicating polyurethane formation, were noted:

Gelation Time—a thickening of the reaction mixture is noticeable: 4 seconds;

Tack-Free Time—the surface of the mixture will not stick to an object: 5 seconds;

Firm Time—the reaction mass will not yield under manual pressure: 6 seconds.

The above data indicate the usefulness of the novel compound as a chain extender especially for reaction injection molding.

The above description and non-limiting examples serve to illustrate the invention but various aspects of the invention may be varied without departing from the scope or spirit thereof as defined by the appended claims.

I claim:

1. A polyurethane formed by reacting an organic polyol, an organic polyisocyanate, and a chain extender comprising the compound 1-methyl-2,6-diamino-3-isopropylbenzene in the presence of a catalyst for the reaction of the polyisocyanate and the polyol.

* * * * *